Figure 1:
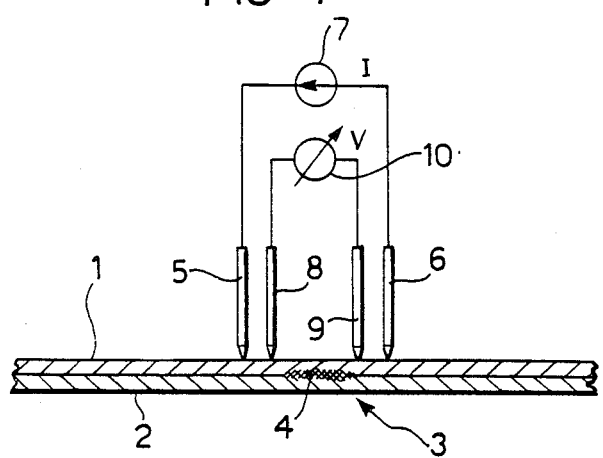

United States Patent [19]

Re Fiorentin et al.

[11] Patent Number: 4,887,025
[45] Date of Patent: Dec. 12, 1989

[54] METHOD AND APPARATUS FOR THE NON-DESTRUCTIVE CHECKING OF SPOT WELDS BETWEEN METAL SHEETS PRODUCED BY ELECTRIC WELDING

[75] Inventors: Stefano Re Fiorentin, Grugliasco; Renzo Gaudenzi, Piossasco, both of Italy

[73] Assignee: Fiat Auto S.p.A., Turin, Italy

[21] Appl. No.: 141,754

[22] Filed: Jan. 11, 1988

[30] Foreign Application Priority Data

Jan. 9, 1987 [IT] Italy .................................. 67011 A/87

[51] Int. Cl.$^4$ ............................................. G01R 27/14
[52] U.S. Cl. ..................................... 324/65 R; 324/62; 324/64
[58] Field of Search ................... 324/65 R, 64, 72, 62; 219/110, 117.1

[56] References Cited

U.S. PATENT DOCUMENTS 3,995,213 11/1976 Robinson et al. ...................... 324/64
4,368,422 1/1983 Bachet et al. ........................... 324/64
4,656,595 4/1987 Hognestad ......................... 324/64 X

FOREIGN PATENT DOCUMENTS 1169711 11/1969 United Kingdom ................. 324/64

OTHER PUBLICATIONS

Pivnichny et al., Four-Point Method Tests Solder Joints, 4-1975, Electronics, vol. 48, No. 7, pp. 106–107.

Primary Examiner—Gerard R. Strecker
Assistant Examiner—Jack B. Harvey
Attorney, Agent, or Firm—Sughrue, Mion, Zinn, Macpeak & Seas

[57] ABSTRACT

An electrical current of predetermined strength is passed through a spot weld by a first pair of electrodes. The electrical potential difference between two points, respectively upstream and downstream of the spot weld along the current path, is measured with a second pair of electrodes. In particular, this second pair of electrodes is used to carry out at least one first measurement before the application of the current, and at least one second measurement during the application of the current. These measurements are carried out at two instants separated by a time interval equal to or a whole multiple of the period of the main power voltage. The difference between the values measured in the first and second measurements provides an indication of the quality of the spot weld.

7 Claims, 2 Drawing Sheets

METHOD AND APPARATUS FOR THE NON-DESTRUCTIVE CHECKING OF SPOT WELDS BETWEEN METAL SHEETS PRODUCED BY ELECTRIC WELDING

The present invention relates to a method for the non-destructive checking of spot welds between metal sheets, produced by electric welding.

In order to check the quality of joints between metal sheets made by electric spot welding, the test most commonly used even today is of a destructive type and consists of the mechanical opening of the join and inspection of the area of the weld point.

However, methods and apparatus for non-destructive checking based on the use of ultrasound have been proposed. These methods of checking, although not allowing the mechanical strength of a spot weld to be evaluated, do allow any cracks, spaces or intrusions to be detected. The acoustic coupling between the ultrasonic transducer and the surface of the spot weld, which is usually somewhat irregular, does remain very problematical, however.

Systems for the radiographic inspection of spot welds have also been proposed but are not very satisfactory; radiographic inspection carried out in the plane of the joint usually has very little significance, while that carried out perpendicular to the plane of the joint does not allow the absence of interfacial fusion between the metal sheets, which is one of the more frequently encountered defects in spot welds, to be detected with certainty.

A method for the non-destructive checking of spot welds has also been proposed in which an electrical current of predetermined constant strength is passed through a spot weld by means of a first pair of electrodes and the electrical potential difference between two points on the surface of one of the metal sheets, respectively upstream and downstream of the spot weld along the path of the current, is measured by means of a second pair of electrodes.

A method of this type is known, for example, from international patent (PCT) application published under the number WO84/04818.

This document describes a method in which a current is passed through a spot weld first in one direction and then in the opposite direction, while the voltage drop which is localised at the spot weld is integrated simultaneously.

This method, like the device for carrying out, is very complicated.

A further disadvantage of the non-destructive method of checking based on the passage of a current through a first pair of electrodes and the detection of the voltage through a second pair of electrodes lies in the fact that these electrodes, and particularly those used for measuring the voltage, may pick up electromagnetic disturbances which can "contaminate" the measurement. In fact, the checking of the spot welds on the production line is carried out close to the welding machines used. These machines, supplied by the main power voltage, generate electromagnetic disturbances of a certain strength, typically at the main power voltage frequency.

An object of the present invention is to provide a non-destructive checking method of the type mentioned above which enables more reliable results to be obtained by the elimination of the disturbing effects.

This object is achieved according to the invention by a method of the type specified above, the main characteristic of which lies in the fact that the second pair of electrodes is used to make at least one first measurement before the application of the current and at least one second measurement made during the application of the current, the first and second measurements being carried out at two instants separated by a time interval equal to or a whole multiple of the period of the main power voltage, the difference between the values measured in the first and second measurements providing an indication of the quality of the spot weld.

According to a further characteristic of the method of the present invention, the current is applied for a period of time typically between 20 and 40 ms, preferably 30 ms. Such a brief duration of the application of the current enables errors in measurement due to heating of the spot weld by the Joule effect to be avoided.

The invention also relates to a device for carrying out the aforesaid method.

Figure 2:
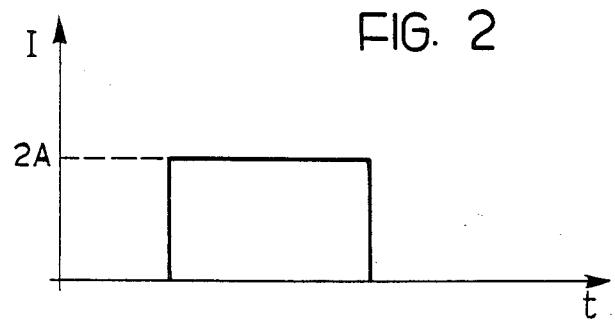
Figure 3:
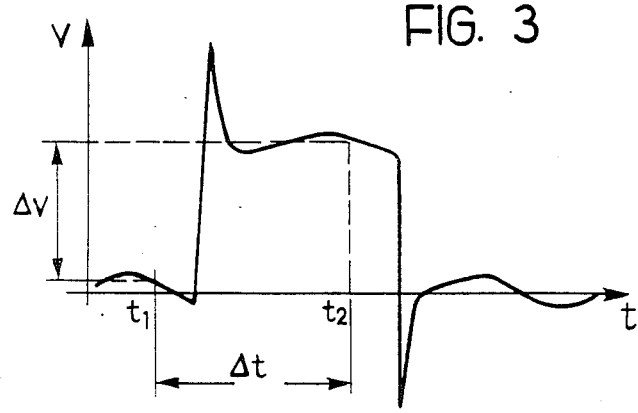
Figure 4:
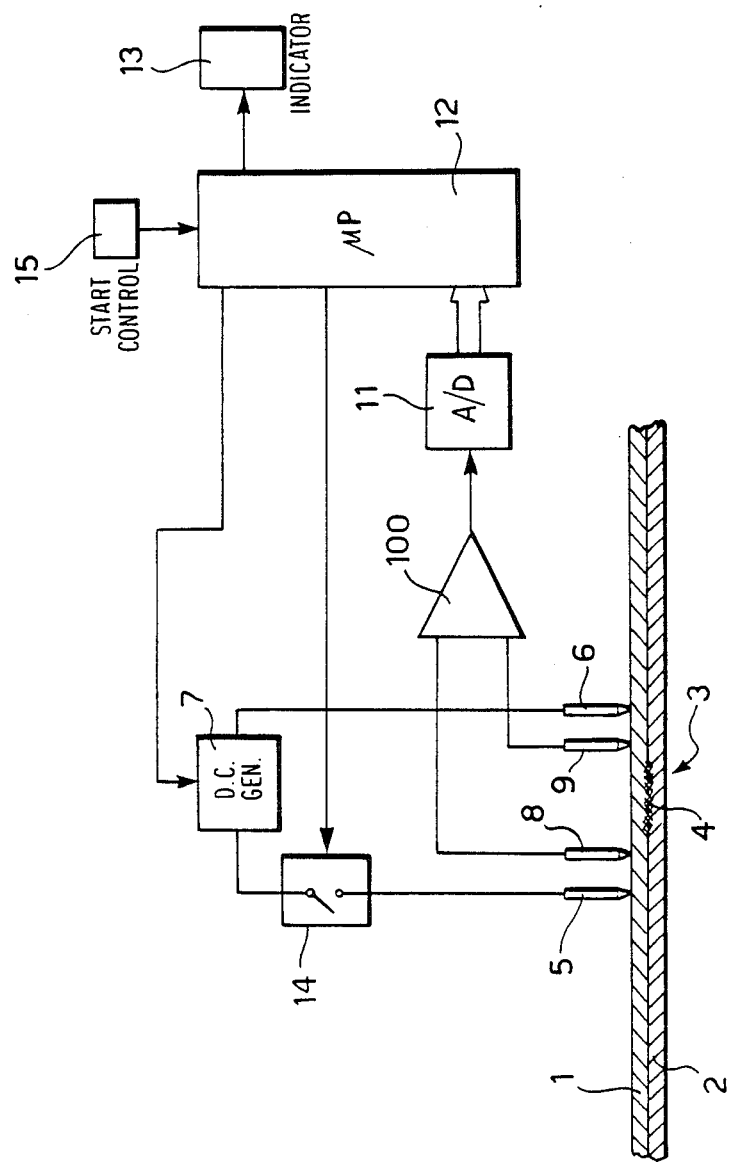

Further characteristics and advantages of the invention will become apparent from the detailed description which follows with reference to the appended drawings, provided purely by way of non-limiting example, in which:

FIG. 1 is a schematic view of apparatus usable in principle for carrying out the method of the invention, FIGS. 2 and 3 are graphs showing the changes in the current I passed through a spot weld and the corresponding detected voltage V as a function of the time t on the abscissa, and FIG. 4 is a block schematic diagram of apparatus usable for carrying out the method of the invention.

In FIG. 1 two metal sheets, indicated 1 and 2, have a spot weld at 3 made by electric welding. The portion of the fused interface which forms the joint between the two sheets is indicated 4.

Two electrodes 5 and 6 are placed in contact with the metal sheet 1 at points such that the spot weld 3 falls on the line joining them. The electrodes 5 and 6 are connected to a direct current generator 7 which generates a current of predetermined strength, for example 2A, when activated.

Two further electrodes 8 and 9 are also placed in contact with the metal sheet 1 along the line joining the electrodes 5 and 6 close to the edges of the spot weld 3. The electrodes 8 and 9 are connected to a voltmeter 10.

In order to check the quality of the spot weld 3 in accordance with the invention, a pulse of current having, for example, the form illustrated in FIG. 2 is passed through the spot weld 3 by means of the generator 7 and the electrodes 5 and 6: this pulse has an amplitude of 2A and a duration of 30 ms starting from an instant $t_o$.

By means of the voltmeter 10, a first voltage measurement is effected at an instant $t_1$ before $t_o$ (FIG. 3) and a subsequent measurement is carried out at an instant $t_2$ during the application of the current pulse. An essential characteristic of the method of the invention is that the time interval between $t_2$ and $t_1$ is equal to the period of the main power voltage (or a multiple thereof, but in this case the pulse must have an adequate duration). If the main power frequency is, for example, 50 Hz, then the interval $\Delta t = t_2 - t_1$ is 20 ms. This choice allows the effects of electromagnetic disturbances at the main power frequency picked up through the electrodes 8 and 9 to be eliminated.

In effect, if the current pulse passed through the spot weld has the shape illustrated in FIG. 2, the voltage detected between the electrodes 8 and 9, apart from transients at the beginning and end, should stabilise at a constant value $\Delta V$. In practice, because of the effect of disturbances picked up, the measurable changes in the voltage V are rather more like those illustrated in FIG. 3: before the beginning and after the end of the current pulse, the voltage V is usually nil. Moreover, the voltage pulse has a "plateau" like that of the current but is also "contaminated" by disturbances picked up.

By virtue of the arrangement mentioned above, the difference $\Delta V$ between the two voltage values measured at the instants $t_1$ and $t_2$ is independent of the disturbances picked up by the electrodes 8 and 9 and depends solely on the characteristics of the spot weld. The difference $\Delta V$ may thus be compared conveniently to the difference $\Delta V_0$ detected in the same manner but with the electrodes 5, 6 and 8, 9 placed in contact with a portion of the metal sheet 1 not including any spot weld. In general, the difference V is less than $\Delta V_0$ In particular, when $\Delta V$ is less than a certain predetermined faction of $\Delta V_0$, the spot weld may be considered as good. Thus, for example, from tests carried out by the applicants, it is found that, with a spot weld having a diameter of 4 mm made by the electric welding of two juxtaposed iron sheets each having a thickness of 0.8 mm, the spot is good if $\Delta V$ is less than 0.8 $\Delta V_0$.

According to the thicknesses and dimensions of the spot welds considered, it is possible to determine experimentally, once and for all, the value of $\Delta V$ which enables acceptable spot welds to be differentiated from unacceptable ones.

FIG. 4 illustrates apparatus for enabling the method described above to be carried out rapidly. In this drawing, the parts and elements already described above have again been given the same reference numerals.

The apparatus illustrated in FIG. 4 comprises a voltage amplifier 100 having its inputs connected to the electrodes 8 and 9 and its output connected to an analogue/digital converter 11. The output of the latter is connected to an electronic microprocessor control and processing unit 12 which controls the operation of the current generator 7 and an indicator device 13. The unit 12 also controls a switch 14 located in series between the electrode 5 and the current generator 7. The switch 14 is normally in the condition in which it prevents current from passing to the electrode 5.

The unit 12 is also connected to a control device 15 which can be operated manually, for example, to start the checking of a spot weld.

In known manner and by conventional techniques, the unit 12 is arranged to acquire and store at least one voltage between the electrodes 8 and 9 before a current pulse produced by the generator 7 is applied to the spot weld. Once this voltage has been measured and stored, the unit 12 switches the switch 14 and activates the current generator 7 to cause a pulse of current to pass through the spot weld, for example, with the characteristics illustrated in FIG. 2. During the application of this current pulse, the unit 12 acquires and stores another voltage measured between the electrodes 8 and 9 after a time interval equal to the period of the main power voltage. The unit 12 voltage then calculates the difference between the two voltage readings taken and activates the indicator device 13 which provides a corresponding indication.

Conveniently, the unit 12 may be arranged to acquire N voltage values between the electrodes 8 and 9 before the application of the current pulse, and N voltage values detected during the application of the current pulse. The instants of acquisition of the 2 N values are selected so that, in practice, the unit acquires N pairs of measured values, each pair comprising one value detected before the application of a current pulse and a second value detected during the application of the current, the first and second values of each pair of measured values in any case being detected at two instants separated by a time interval equal to or a multiple of the period of the main power voltage. The unit 12 calculates the difference between the two measured values of each pair and then calculates the average of these N differences. This average value is then compared with a previously stored reference value and the result of the check on the spot weld indicated by means of the device 13.

The method and apparatus according to the invention are extremely simple. The results obtainable are very reliable.

We claim:

1. A method for the non-destructive checking of a spot weld between metal sheets, produced by electric welding, in which an electrical direct current of predetermined constant strength is passed through a spot weld by means of a first pair of electrodes and the electrical potential difference between two points on the surface of one of the sheets, respectively upstream and downstream of the spot weld along the path of the current, is measured by means of a second pair of electrodes, the second pair of electrodes being used to make at least one first measurement before the application of the direct current and at least one second measurement during the application of the direct current, the first and second measurements being carried out at two instants separated by a time interval equal to or a whole multiple of the period of the main power voltage used for electric welding, the difference between the values measured in the first and second measurements providing an indication of the quality of the spot weld.

2. A method according to claim 1, wherein a plurality of pairs of measurement is effected, each of which comprises one measurement carried out before the application of the current and a second measurement carried out during the application of the current, the measurements of each pair of measurements being carried out at instants separated by a time interval equal to or a multiple of the period of the main power voltage, the average of the difference between the values measured in the pairs of measurements providing an indication of the quality of the spot weld.

3. A method according to claim 2, wherein the current is applied for a first period of time of between 20 and 40 ms.

4. A method according to claim 3, wherein the current has a strength of between 1 and 4 A.

5. An apparatus for the non-destructive checking of a spot weld between metal sheets, produced by electric welding, comprising
a direct current generator,
a first pair of electrodes connected to the generator for passing an electrical current of predetermined strength through a spot weld in use,
voltage measuring means,
a second pair of electrodes connected to the measuring means for detecting the electrical potential difference between two points on the surface of one of the metal sheets, respectively upstream and downstream of the spot weld along the path of the current, an indicator device, and an electronic control unit connected to the current generator, the voltage measuring means and the indicator device, and arranged:
- to detect and store at least one value of the voltage detected by the measuring means between the two points at a first instant before the application of the current to the spot weld,
- to cause the application of the current produced by the generator through the first pair of electrodes for a predetermined period of time,
- to detect and memorize at least one value of the voltage measured by the measuring means during the application of the current, at a second instant separated from the first instant by a time interval equal to or a whole multiple of the period of the main power voltage used for the electric welding;
- to generate electrical signals indicative of the difference between the voltages detected at the first and second instants, and
- to activate the indicator device so as to provide a perceptible indication of the difference.

6. An apparatus according to claim 5, wherein the unit is arranged to acquire and store a plurality of pairs of voltage values detected by the measuring means, each of which comprises one value detected before the application of the current and a second value detected during the application of the current, the first and second values of each pair of voltage values being detected at respective instants separated by a time interval equal to or a multiple of the period of the main power voltage, the unit also being arranged to calculate the average of the differences between the measured values in the pairs of measurements.

7. An apparatus according to claim 6, including:
- a controlled switch connected in series with the current generator between the electrodes of the first pair of electrodes,
- a voltage amplifier having its inputs connected to the second pair of electrodes,
- an analogue/digital converter connected to the output of the amplifier, and
- a microprocessor unit connected to the current generator, the command input of the controlled switch, the output of the analogue/digital converter, and the indicator device.

* * * * *